United States Patent
Cho et al.

(12)

(10) Patent No.: US 9,941,114 B2
(45) Date of Patent: Apr. 10, 2018

(54) ORGANOMETALLIC PRECURSORS AND METHODS OF FORMING THIN LAYERS USING THE SAME

(71) Applicant: Samsung Electronics Co., Ltd., Suwon-Si, Gyeonggi-Do (KR)

(72) Inventors: Youn-Joung Cho, Hwaseong-si (KR); Youn-Soo Kim, Yongin-si (KR); Sang-Jun Yim, Cheongju-si (KR); Myong-Woon Kim, Daejeon (KR); Sang-Ick Lee, Daejeon (KR); Sang-Chul Youn, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 528 days.

(21) Appl. No.: 14/611,691

(22) Filed: Feb. 2, 2015

(65) Prior Publication Data

US 2015/0255276 A1 Sep. 10, 2015

(30) Foreign Application Priority Data

Mar. 10, 2014 (KR) ........................ 10-2014-0027671

(51) Int. Cl.
*H01L 21/02* (2006.01)
*H01L 23/00* (2006.01)
*C07F 7/00* (2006.01)
*H01L 23/29* (2006.01)
*H01L 23/31* (2006.01)
*C23C 16/40* (2006.01)
*C23C 16/455* (2006.01)
*H01L 49/02* (2006.01)

(52) U.S. Cl.
CPC .......... *H01L 21/0228* (2013.01); *C07F 7/006* (2013.01); *C23C 16/405* (2013.01); *C23C 16/45553* (2013.01); *H01L 21/02189* (2013.01); *H01L 23/291* (2013.01); *H01L 23/3171* (2013.01); *H01L 28/40* (2013.01); *H01L 2924/0002* (2013.01)

(58) Field of Classification Search
None
See application file for complete search history.

(56) References Cited

U.S. PATENT DOCUMENTS

| | | | |
|---|---|---|---|
| 6,383,669 B1 | 5/2002 | Leedham et al. |
| 6,403,735 B1 | 6/2002 | Becke et al. |
| 6,870,017 B2 | 3/2005 | Nabika et al. |
| 7,005,392 B2 | 2/2006 | Baum et al. |
| 7,704,895 B2 | 4/2010 | Lavoie et al. |
| 7,727,910 B2 | 6/2010 | Ahn et al. |
| 7,754,621 B2 | 7/2010 | Putkonen |
| 8,003,814 B2 | 8/2011 | Wada et al. |
| 8,309,747 B2 | 11/2012 | Yang et al. |
| 8,568,530 B2 | 10/2013 | Heys et al. |
| 2007/0031599 A1 | 2/2007 | Gschwandtner et al. |
| 2010/0112211 A1 | 5/2010 | Xu et al. |
| 2010/0270508 A1 | 10/2010 | Xu et al. |
| 2010/0290945 A1 | 11/2010 | Ma |
| 2012/0196449 A1 | 8/2012 | Xu et al. |

FOREIGN PATENT DOCUMENTS

| JP | 2007-527621 A | 9/2007 |
|---|---|---|
| JP | 2010-189313 A | 9/2010 |
| JP | 4903773 B2 | 3/2012 |
| JP | 2012-526811 A | 11/2012 |
| KR | 2001-0031855 | 4/2001 |
| KR | 2002-0000120 A | 1/2002 |
| KR | 2007-0114696 A | 12/2007 |
| KR | 100804413 B1 | 2/2008 |
| KR | 2008-0025301 A | 3/2008 |
| KR | 2008-0075177 A | 8/2008 |
| KR | 2010-0016477 A | 2/2010 |
| KR | 2010-0117500 A | 11/2010 |

*Primary Examiner* — Kamal Saeed
(74) *Attorney, Agent, or Firm* — Harness, Dickey & Pierce, P.L.C.

(57) ABSTRACT

An organometallic precursor is represented by a chemical formula of $X_n(M)(R1)_m(R2)_k$. M is a central metal. X is a ligand of M and one of 6,6-dimethylfulvenyl, indenyl, cyclopentadienyl and cyclopentadienyl substituted with an amino group. R1 and R2 are ligands of M, and each independently an amino group or an ethylenediamino group. Each n, m and k is a positive integer, and a sum of n, m and k is equal to 3 or 4.

20 Claims, 8 Drawing Sheets

ORGANOMETALLIC PRECURSORS AND METHODS OF FORMING THIN LAYERS USING THE SAME

CROSS-REFERENCE TO RELATED APPLICATION

This application claims priority under 35 USC § 119 from Korean Patent Application No. 10-2014-0027671, filed on Mar. 10, 2014 in the Korean Intellectual Property Office (KIPO), the contents of which are incorporated by reference herein in their entirety.

BACKGROUND

1. Field

Example embodiments relate to organometallic precursors and/or methods of forming thin layers using the same. More particularly, example embodiments relate to organometallic precursors for a deposition process and/or methods of forming thin layers using the same.

2. Description of the Related Art

To improve electrical characteristics of a semiconductor device, a thin layer having a high dielectric constant and a low resistance may be needed. The thin layer may be formed using an organometallic precursor by a chemical vapor deposition (CVD) process or an atomic layer deposition (ALD) process.

However, the deposition processes may be performed at a high temperature and cause thermal decomposition of the organometallic precursor, and thus the thin layer formed therefrom may have defects. Particularly, if the thin layer is formed in an opening having a high aspect ratio, defects of the thin layer may be exacerbated due to poor step coverage.

SUMMARY

Example embodiments relate to an organometallic precursor having improved thermal and/or chemical properties.

Example embodiments relate to a method of forming a thin layer from an organometallic precursor having improved thermal and/or chemical properties.

Example embodiments relate to an organometallic precursor represented by Chemical Formula 1 below:

[Chemical Formula 1]

In Chemical Formula 1, M is a central metal. X is a ligand of M and may include one of 6,6-dimethylfulvenyl, indenyl, cyclopentadienyl and cyclopentadienyl substituted with an amino group. R1 and R2 are ligands of M, and each independently an amino group or an ethylenediamino group. Each n, m and k is a positive integer, and a sum of n, m and k is equal to 3 or 4.

In example embodiments, the central metal may be one of zirconium, hafnium and titanium.

In example embodiments, the amino group and the ethylenediamino group of R1 and R2 may each independently include a $C_1$-$C_4$ alkyl substituent In example embodiments, X may be 6,6-dimethylfulvenyl or indenyl. R1 and R2 may be each independently the amino group. In this case, n may be 1, and a sum of m+k may be equal to 3.

In example embodiments, X is cyclopentadienyl substituted with the amino group, and X is a multidentate ligand.

In example embodiments, the organometallic precursor may be represented by Structural Formula 1 illustrated below:

[Structural Formula 1]

In Structural Formula 1, M may be a central metal, R3 and R4 may be each independently methyl or ethyl, and R5 may be a $C_1$-$C_4$ alkyl.

In example embodiments, R1 may be the amino group, R2 may be the ethylenediamino group, and each n, m and k may be 1.

In example embodiments, the organometallic precursor may be represented by Structural Formula 2 Illustrated below:

[Structural Formula 2]

In Structural Formula 2, M may be a central metal, R3 and R4 may be each independently methyl or ethyl, and R6 may be a C1-C4 alkyl.

According to example embodiments, there is provided a method of forming a thin layer. In the method, a deposition source including an organometallic precursor represented by Chemical Formula 1 is provided on a substrate. A reactive gas is provided on the substrate to react with the deposition source.

[Chemical Formula 1]

In Chemical Formula 1, M is a central metal. X is a ligand of M and may include one of 6,6-dimethylfulvenyl, indenyl, cyclopentadienyl and cyclopentadienyl substituted with an amino group. R1 and R2 are ligands of M, and each independently an amino group or an ethylenediamino group. Each n, m and k is a positive integer, and a sum of n, m and k is equal to 3 or 4.

In example embodiments, the central metal may be one of zirconium, hafnium and titanium.

In example embodiments, the deposition source may include at least two of the organometallic precursors, the central metals of which may be different from each other.

In example embodiments, the deposition source may further include a silicon compound.

In example embodiments, the reactive gas may include an oxidizing agent, a reducing agent and a nitridating agent. These may be used alone or in a combination thereof.

In example embodiments, the reactive gas and the deposition source may react with each other at a temperature ranging from about 200° C. to about 325° C.

In example embodiments, the organometallic precursor may include at least one of the compounds represented by Structural Formulas 1 to 4 Illustrated below:

[Structural Formula 1]

[Structural Formula 2]

[Structural Formula 3]

[Structural Formula 4]

In Structural Formulas 1 to 4, M may be a central metal, R3 and R4 may be each independently methyl or ethyl, and R5 and R6 may be each independently a $C_1$-$C_4$ alkyl.

Example embodiments relate to a deposition structure including a substrate, a deposition layer on the substrate, the deposition layer obtained from an organometallic precursor represented by the following formula, $X_n(M)(R1)_m(R2)_k$, M being a metal, X being a ligand of M and one of 6,6-dimethylfulvenyl, indenyl, cyclopentadienyl and cyclopentadienyl substituted with an amino group, R1 and R2 being ligands of M, and each independently being an amino group or an ethylenediamino group, each one of n, m and k being a positive integer, and a sum of n, m and k is equal to one of 3 and 4.

As described above, an organometallic precursor in accordance with example embodiments may have improved chemical stability, storage stability, volatility, thermal stability and step coverage. Thus, the organometallic precursor may be utilized as a deposition source in a CVD process and in an ALD process so that a uniform thin layer may be formed even in an opening having a high aspect ratio.

BRIEF DESCRIPTION OF THE DRAWINGS

Example embodiments will be more clearly understood from the following detailed description taken in conjunction with the accompanying drawings. FIGS. 1 to 11 represent non-limiting, example embodiments as described herein.

DESCRIPTION OF EXAMPLE EMBODIMENTS

Various example embodiments will be described more fully hereinafter with reference to the accompanying drawings, in which some example embodiments are shown. The present inventive concepts may, however, be embodied in many different forms and should not be construed as limited to the example embodiments set forth herein. Rather, these example embodiments are provided so that this description will be thorough and complete, and will fully convey the scope of the present inventive concepts to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

It will be understood that, although the terms first, second, third, fourth etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concepts.

In the drawing figures, the dimensions of layers and regions may be exaggerated for clarity of illustration. Like reference numerals refer to like elements throughout. The same reference numbers indicate the same components throughout the specification.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present inventive concepts. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concepts.

Unless otherwise defined, all terms (including technical and scientific terms) used herein have the same meaning as commonly understood by one of ordinary skill in the art to which these inventive concepts belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

Organometallic Precursors

An organometallic precursor may be represented by Chemical Formula 1 illustrated below. The organometallic precursor may have improved chemical stability, storage stability, volatility, thermal stability and step coverage. Thus, the organometallic precursor may be utilized as a deposition source in a chemical vapor deposition (CVD) process and an atomic layer deposition (ALD) process.

[Chemical Formula 1]

$X_n(M)(R1)_m(R2)_k$

In Chemical Formula 1, M may represent a central metal, and X may represent a ligand of M. X may be one of 6,6-dimethylfulvenyl, indenyl, cyclopentadienyl and cyclopentadienyl substituted with an amino group. R1 and R2 are ligands of M, and may each independently be an amino group or an ethylenediamino group. For example, each n, m and k is a positive integer, and a sum of n, m and k may be equal to 3 or 4.

The central metal may include zirconium (Zr), hafnium (Hf) or titanium (Ti)

The amino group and the ethylenediamino group of R1 and R2 may include at least one $C_1$-$C_4$ alkyl substituent. Accordingly, the amino group may be a dialkylamino group including methyl and/or ethyl. The ethylenediamino group may be N,N'-dialkylethyleneamino group including a $C_1$-$C_4$ alkyl substituent.

In example embodiments, the organometallic precursor may be represented by the following Structural Formula 1. In the corresponding Chemical Formula 1, X may be cyclopentadienyl substituted with an amino group and may serve as a multidendate ligand.

[Structural Formula 1]

In Structural Formula 1, M may represent a central metal, R3 and R4 may each independently be methyl or ethyl, and R5 may be a $C_1$-$C_4$ alkyl.

In an example embodiment, the organometallic precursor may be represented by the following Structural Formula 2. In the corresponding Chemical Formula 1, X may be cyclopentadienyl, R1 may be an amino group, and R2 may be an ethylenediamino group. Each n, m and k may be 1.

[Structural Formula 2]

In Structural Formula 2, M may represent a central metal, R3 and R4 may each independently be methyl or ethyl, and R6 may be a $C_1$-$C_4$ alkyl.

In an example embodiment, the organometallic precursor may be represented by the following Structural Formula 3 or Structural Formula 4. In the corresponding Chemical Formula 1, X may be 6,6-dimethylfulvenyl or indenyl, R1 and R2 may each be an amino group, n may be 1, and a sum of m and k is equal to 3.

[Structural Formula 3]

[Structural Formula 4]

In Structural Formulas 3 and 4, M may represent a central metal, and R3 and R4 may each independently be methyl or ethyl.

In the Structural Formulas 1 to 4, hydrogen may be combined to nitrogen (N), however, an illustration of hydrogen is omitted for brevity.

The organometallic precursor may be prepared by reacting a first compound represented by Chemical Formula 2 below with 6,6-dimethylfulvenyl, indenyl, cyclopentadienyl or cyclopentadienyl substituted with an amino group. Alternatively, the organometallic precursor may be prepared by reacting a second compound represented by Chemical Formula 3 with a third compound represented by Chemical Formula 4.

(M)(NR3R4)$_4$     [Chemical Formula 2]

(C$_5$H$_6$)(M)(NR3R4)$_3$     [Chemical Formula 3]

In Chemical Formulas 2 and 3, M may be a central metal and one of zirconium (Zr), hafnium (Hf) or titanium (Ti), and R3 and R4 may each independently be methyl or ethyl.

(C$_2$H$_4$)(NHR6)$_2$     [Chemical Formula 4]

In Chemical Formula 4, R6 may be a C$_1$-C$_4$ alkyl.

Example 1

Dimethylamine (NH(CH$_3$)$_2$) is added to a solution including n-butyllithium hexane at about −30° C., cooled to a room temperature and stirred for a day to form lithiumdimethylamine (LiN(CH$_3$)$_2$). Zirconium tetrachloride (ZrCl$_4$) is added to a resultant solution at about −30° C. and stirred for a day. A solvent and volatile by-products are removed by a distillation under a reduced pressure to obtain tetrakis dimethyamino zirconium (Zr(N(CH$_3$)$_2$)$_4$). The resultant tetrakis dimethyamino zirconium is cooled to about −30° C. in a hexane solution, and then 6,6-dimethylfulvene is added at a room temperature and stirred for a day. A solvent and volatile by-products are removed by a distillation under a reduced pressure to obtain an organometallic precursor represented by the following Structural Formula 5.

[Structural Formula 5]

Example 2

Processes substantially the same as those of Example 1 are performed except that methylethylamine (NH(CH$_3$)(C$_2$H$_5$)) is used instead of dimethylamine to form lithium methylethylamine (LiN(CH$_3$)(C$_2$H$_5$)) and tetrakis methylethylamino zirconium (Zr(N(CH$_3$)(C$_2$H$_5$))$_4$). Thus, an organometallic precursor represented by the following Structural Formula 6 is prepared.

[Structural Formula 6]

Example 3

Processes substantially the same as those of Example 1 are performed except that indene is used instead of 6,6-dimethylfulvene to form an organometallic precursor represented by the following Structural Formula 7.

[Structural Formula 7]

Example 4

Processes substantially the same as those of Example 1 are performed except that cyclopentadiene substituted with an amino group is used instead of 6,6-dimethylfulvene to form an organometallic precursor represented by the following Structural Formula 8.

[Structural Formula 8]

Example 5

Cyclopentadienyl-tris(dimethylamino) zirconium ($((C_5H_6)Zr(N(CH_3)_2)_3$) is added in a hexane solution and cooled to at about −30° C., and N,N'-dimethylethylenediamine is added to be stirred at a room temperature for a day. A solvent and volatile by-products are removed under a reduced pressure and sublimed to obtain an organometallic precursor represented by the following Structural Formula 9.

[Structural Formula 9]

Methods of Forming Thin Layers

FIGS. 1 to 4 are cross-sectional views illustrating a method of forming a thin layer in accordance with example embodiments. The thin layer may be formed using organometallic precursors in accordance with example embodiments by an ALD process or a CVD process.

Figure 1:
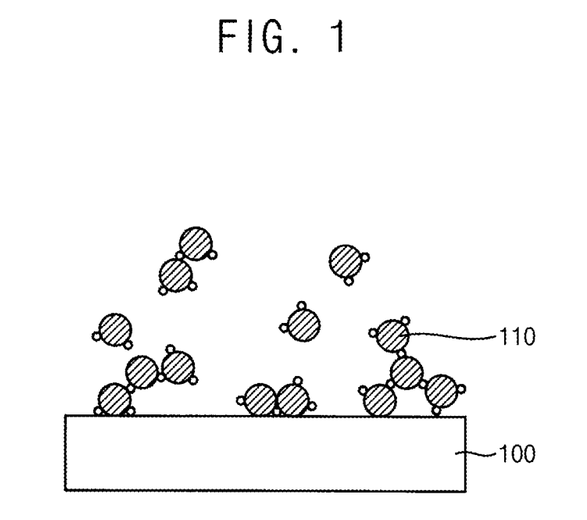
FIGS. 1 to 4 are cross-sectional views illustrating a method of forming a thin layer in accordance with example embodiments.

Referring to FIG. 1, a deposition source 110 may be provided into a chamber including a substrate 100 therein. The deposition source 110 may include the organometallic precursor in accordance with example embodiments.

The deposition source 100 may be vaporized at a temperature ranging from, e.g., about 25° C. to about 400° C. to be provided on the substrate 100 together with a carrier gas including an inert gas such as argon (Ar), helium (He) or nitrogen ($N_2$). In example embodiments, the organometallic precursor may have a great volatility and may be stable at a high temperature, and thus may not be thermally decomposed even at a high deposition temperature to be adsorbed on a top surface of the substrate 100.

In an example embodiment, the deposition source 110 may further include a silicon compound and/or another organometallic precursor having a different central metal according to types of the thin layer. In this case, the organometallic precursor, the silicon compound and the other organometallic precursor may be independently vaporized, or mixed and vaporized together. The silicon compound may include, e.g., silane ($SiH_4$).

Figure 2:
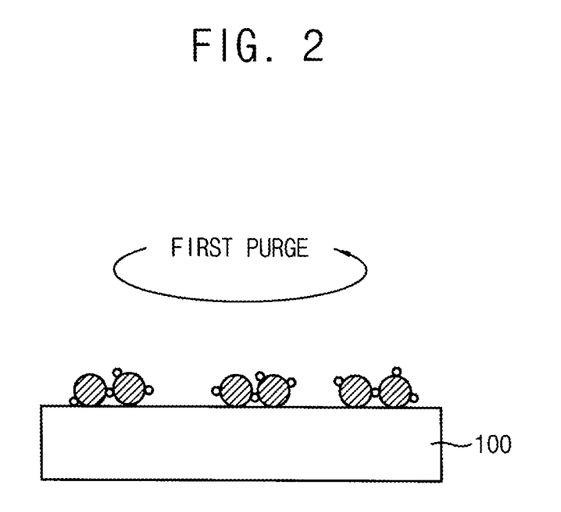

Referring to FIG. 2, a first purge process may be performed on the substrate 100. A portion of the deposition source 110 that may not be adsorbed on the substrate 100, and by-products therefrom, may be removed from the chamber by the first purge process.

The first purge process may include an evacuation using an inert gas such as helium or argon, and/or a pressure reduction.

As for the evacuation, the inert gas may be introduced into the chamber at a flow rate ranging from about 200 sccm to about 5,000 sccm, in one example embodiment, from about 500 sccm to about 2,000 sccm.

As for the pressure reduction, the pressure in the chamber may be reduced to a level of about 0.01 Pa to about 300 Pa, in one example embodiment, about 0.01 Pa to about 100 Pa.

Figure 3:
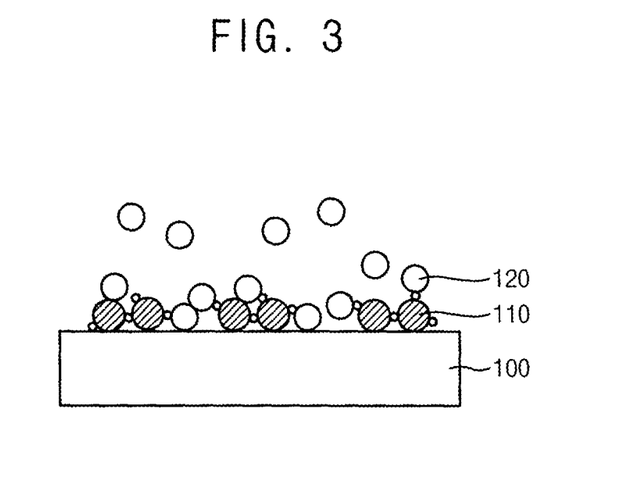

Referring to FIG. 3, a reactive gas 120 may be provided on the substrate 100 to react with the deposition source 110 adsorbed thereon. Thus, a product of the reaction may be deposited on the substrate 100 in the form of a thin layer 130 illustrated in FIG. 4.

The reactive gas 120 may include an oxidizing agent such as oxygen ($O_2$), ozone ($O_3$), nitrogen dioxide ($NO_2$), nitrogen monoxide (NO), hydrogen peroxide ($H_2O_2$), formic acid, acetic acid and acetic anhydride, a reducing agent such as hydrogen ($H_2$), an organic amine compound such as monoalkylamine, trialkylamine and alkylenediamine, a nitridating agent such as hydrazine and ammonia, or an combination thereof.

Figure 4:
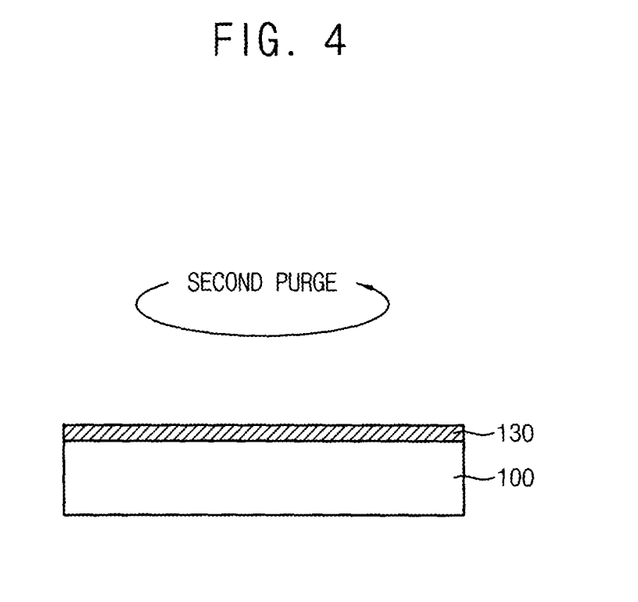

Thus, the thin layer 130 may include a metal layer, a metal oxide layer, a metal nitride layer, a metal oxynitride layer, a metal complex oxide layer, a metal complex nitride layer, a metal complex oxynitride layer, or a combination thereof.

In example embodiments, a composition of the thin layer 130 may be represented by $MSi_xO_y$, $AlM_xSiO_y$, $TiM_xSiO_y$, $HfM_xSiO_y$, $MN_xO_y$, $AlM_xNO_y$, $TiM_xNO_y$ or $HfM_xNO_y$. Here, M may be zirconium, titanium or hafnium, and x and y are not specifically limited herein.

The reaction between the deposition source 110 and the reactive gas 120 may occur at a temperature ranging from about 200° C. to about 400° C., in an example embodiment, from about 200° C. to about 325° C. If the temperature is less than about 200° C., the reaction may not be initiated. If the temperature exceeds about 400° C., the deposition source may be thermally decomposed. In an example embodiment, an additional energy such as plasma, light, voltage may be further provided on the substrate 100 to activate the reaction.

Referring to FIG. 4, a process substantially the same as or similar to or the same as the process illustrated with reference to FIG. 2 may be performed. Thus, the second purge process may include an evacuation using an inert gas such as helium or argon, and/or a pressure reduction. Accordingly, a second purge may be performed so that a portion of the reactive gas 120 that is not transformed into the thin layer 130, and by-products of the reaction, may be removed from the chamber.

The processes illustrated above may be repeated as a plurality of cycles until a desired, or alternatively predetermined, thickness of the thin layer 130 is achieved.

In an example embodiment, a structure including a recess or a contact hole may be formed on the substrate 100, and the thin layer may be formed on an innerwall of the recess or the contact hole. Alternatively, the thin layer may be formed to fill the recess or the contact hole. In this case, a reflow process may be further performed to improve step coverage of the thin layer.

As described above, the organometallic precursor according to example embodiments may be used as the deposition source 110. The organometallic precursor may have a great volatility and a high thermal stability, and thus the thin layer 130 may be easily formed by an ALD process or a CVD process. The organometallic precursor may also have improved step coverage, and thus the thin layer 130 may be formed substantially uniformly on a structure having a high aspect ratio such as a concave surface.

The types of deposition source 110 and of reactive gas 120 may be properly selected according to types of the thin layer 130. Thus, a desired thin layer may be formed by a CVD process or an ALD process. The thin layer may be implemented as, e.g., a gate insulation layer of a transistor, a dielectric layer of a capacitor or a wiring of a semiconductor device.

Experimental Example 1

A substrate was loaded in a chamber and heated to about 325° C. An organometallic precursor of Example 1 was evaporated at a temperature of about 120° C. and introduced into the chamber for 3 seconds. An argon gas was introduced into the chamber at a flow rate of 300 sccm for 12 seconds to evacuate the chamber, and ozone was introduced into the chamber for 6 seconds at a flow rate of 500 sccm to be reacted with the organometallic precursor. Argon gas was introduced at a flow rate of 500 sccm for 10 seconds to evacuate the chamber. 100 cycles of the processes above were repeated to form a thin layer including a zirconium oxide and having a thickness about 150 Å.

Experimental Example 2

Processes substantially the same as or similar to the processes of Experimental Example 1 except that an organometallic precursor of Example 3 was used to form a thin layer including a zirconium oxide and having a thickness about 100 Å.

Methods of Manufacturing Semiconductor Devices

FIGS. 5 to 10 are cross-sectional views illustrating a method of manufacturing a semiconductor device in accordance with example embodiments.

Figure 5:
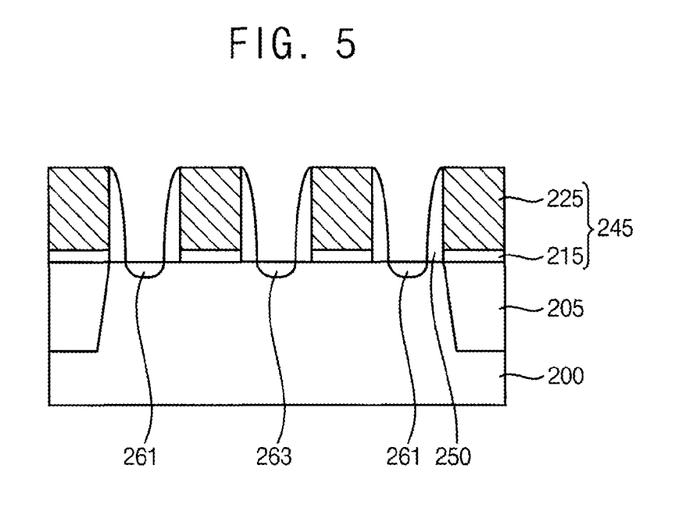
FIGS. 5 to 10 are cross-sectional views illustrating a method of manufacturing a semiconductor device in accordance with example embodiments.

Referring to FIG. 5, a gate structure 245 may be formed on a substrate 200 including an isolation layer pattern 205. A gate spacer 250 may be formed on a sidewall of the gate structure 245. First and second impurity regions 261 and 263 may be formed at upper portions of the substrate 200 adjacent to the gate structure 245. A transistor may be defined by the gate structure 245 and the impurity regions 261 and 263. The first and second impurity regions 261 and 263 may serve as source/drain regions.

The substrate 200 may include a silicon substrate, a germanium substrate, a silicon-germanium substrate, a silicon-on-insulator (SOI) substrate, a germanium-on-insulator (GOI) substrate, or the like.

An isolation layer pattern 205 may be formed by a shallow trench isolation (STI) process. The isolation layer pattern 205 may include silicon oxide.

The gate structure 245 may include a gate insulation layer pattern 215 and a gate electrode 225 sequentially stacked on the substrate 200. For example, a gate insulation layer, a gate electrode layer and a gate mask (not illustrated) may be sequentially formed on the substrate 200. The gate electrode layer and the gate insulation layer may be partially etched using the gate mask to form the gate electrode 225 and the gate insulation layer pattern 215. The gate insulation layer may be formed using an oxide such as silicon oxide. The gate electrode layer may be formed using doped polysilicon or a metal, e.g., tungsten.

A spacer layer covering the gate structure 245 may be formed on the substrate 200, and then may be anisotropically etched to form the gate spacer 250. The spacer layer may be formed using silicon nitride.

An Ion-implantation process may be performed using the gate structure as an implantation mask to form the first and second impurity regions 261 and 263. The first and second impurity regions 261 and 263 may include n-type impurities such as phosphorous or arsenic, or p-type impurities such as boron or gallium.

Figure 6:
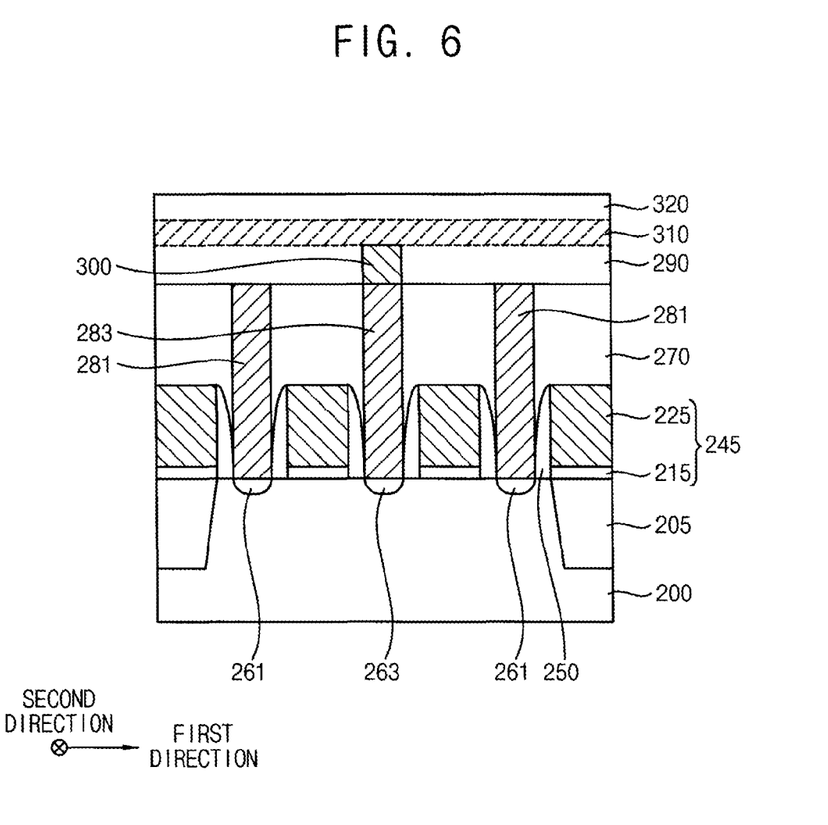

Referring to FIG. 6, a first insulating interlayer 270 covering the gate structures 245 may be formed on the substrate 200. First and second plugs 281 and 283 may be formed through the first insulating interlayer 270 to be in contact with the first and second impurity regions 261 and 263, respectively.

The first insulating interlayer 270 may be formed using silicon oxide such as boro phospho silicate glass (BPSG), undoped silicate glass (USG), silicon on glass (SOG), etc.

In example embodiments, the first insulating interlayer 270 may be partially removed to form first openings through which the first and second impurity regions 261 and 263 are exposed. A first conductive layer sufficiently filling the first openings may be formed on the first insulating interlayer 270, and then an upper portion of the first conductive layer may be planarized until a top surface of the first insulating interlayer 270 is exposed to form the first and second contacts 281 and 283. The first and second plugs 281 and 283 may be electrically connected to the transistor via the first and second impurity regions 261 and 263. The first conductive layer may be formed using doped polysilicon or a metal such as tungsten.

A second insulating interlayer 290 may be formed on the first insulating interlayer 270, and the first and second plugs 281 and 283. A bit line contact 300 may be formed through the second insulating interlayer 290 to be in contact with the second plug 283, and a bit line 310 may be formed on the second insulating interlayer 290 to be electrically connected to the bit line contact 300. A third insulating interlayer 320 covering the bit line 310 may be formed on the second insulating interlayer 290. Thus, the bit line 310 may be electrically connected to the transistor.

In example embodiments, the second insulating interlayer 290 may be partially removed to form a second opening through which the second plug 283 is at least partially exposed. A second conductive layer sufficiently filling the second opening may be formed on the second insulating interlayer 290, and then an upper portion of the second conductive layer may be planarized until a top surface of the second insulating interlayer 290 is exposed to form the bit line contact 300.

In example embodiments, a third conductive layer may be formed on the bit line contact 300 and the second insulating interlayer 290, and may be patterned to form the bit line 310. For example, the bit line 310 may extend in a first direction parallel to a top surface of the substrate 200. A plurality of the bit lines 310 may be arranged along a second direction parallel to the top surface of the substrate 200 and substantially perpendicular to the first direction.

The second and third conductive layers may be formed using doped polysilicon or a metal. The second and third insulating interlayers 290 and 320 may be formed using silicon oxide such as BPSG, USG, SOG, etc.

Figure 7:
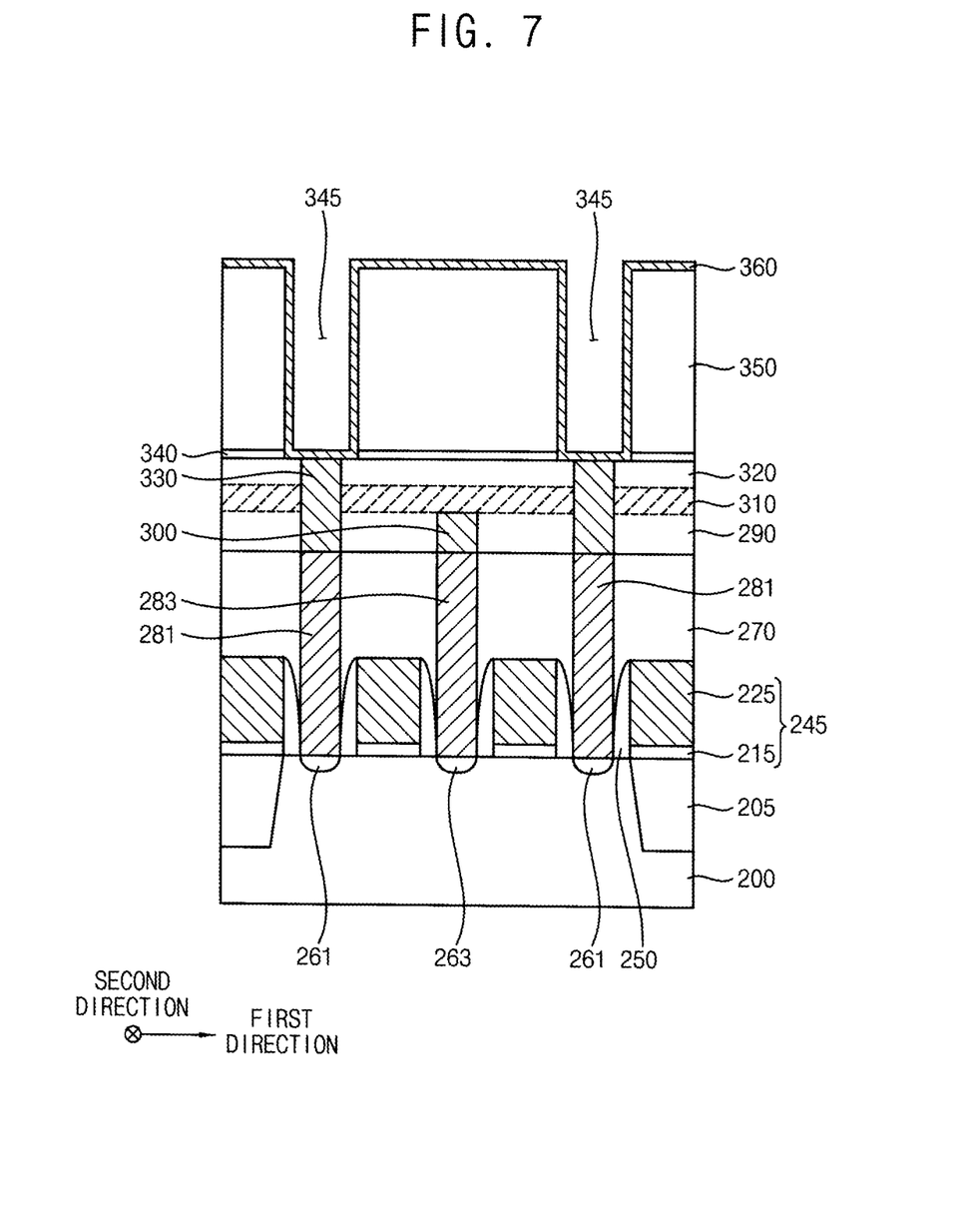

Referring to FIG. 7, a capacitor contact 330 may be formed through the second and third insulating interlayers 290 and 320 to be in contact with the first plug 281.

For example, the second and third insulating interlayers 290 and 320 may be partially removed to form a third opening through which a top surface of the first plug 281 is at least partially exposed. A fourth conductive layer sufficiently filling the fourth opening may be formed on the third insulating interlayer 320. An upper portion of the fourth conductive layer may be planarized until a top surface of the third insulating interlayer 320 is exposed to form the capacitor contact 330. The fourth conductive layer 330 may be formed using doped polysilicon or a metal.

An etch-stop layer 340 and a mold layer 350 may be sequentially formed on the capacitor contact 330 and the third insulating interlayer 320.

The etch-stop layer 340 may be formed using, e.g., silicon nitride. The mold layer 350 may be formed using, e.g., silicon oxide.

The mold layer 350 and the etch-stop layer 340 may be partially removed to form a fourth opening 345 through which a top surface of the capacitor contact 330 is at least partially exposed. A lower electrode layer 360 may be formed on a sidewall and a bottom of the fourth opening 345, and on a top surface of the mold layer 350.

The lower electrode layer 360 may include a metal such as tungsten, titanium or tantalum, or a metal nitride such as tungsten nitride, titanium nitride or tantalum nitride.

Figure 8:
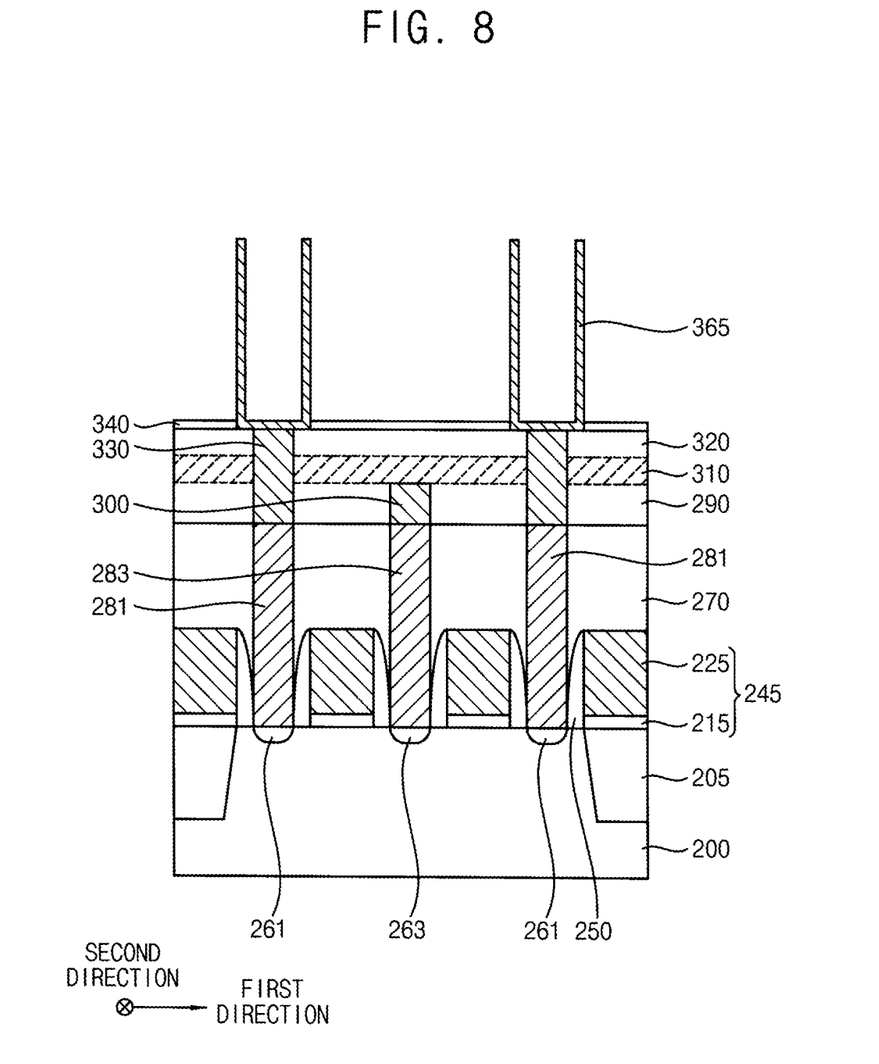

Referring to FIG. 8, a sacrificial layer (not illustrated) sufficiently filling the fourth opening 345 may be formed on the lower electrode layer 360. Upper portions of the sacrificial layer and the lower electrode layer 360 may be planarized until a top surface of the mold layer 350 is exposed to form a lower electrode 365.

The mold layer 350 and the sacrificial layer may be removed by, e.g., a wet etching process. The lower electrode 365 may remain on the capacitor contact 330 and may have a cup shape or a cylindrical shape.

Figure 9:
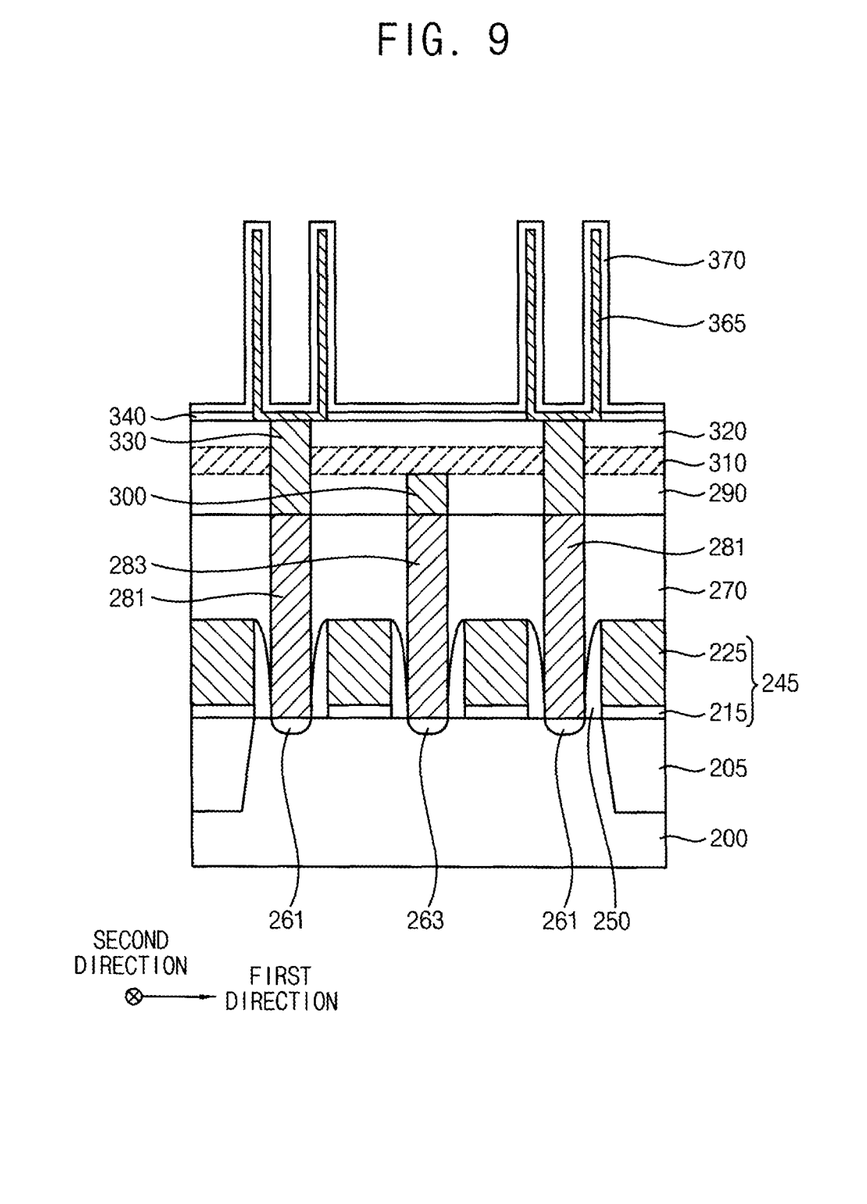

Referring to FIG. 9, processes substantially the same as or similar to the processes illustrated with reference to FIGS. 1 to 4 may be performed to form a dielectric layer 370 on the etch-stop layer 340 and the lower electrode 365.

The dielectric layer 370 may be formed using an organometallic precursor in accordance with example embodiments. Accordingly, the dielectric layer 370 may contain a metal ingredient including zirconium, hafnium, titanium and/or aluminum and may have a high dielectric constant. Even though an aspect ratio of the lower electrode 365 is increased, the dielectric layer 370 may be formed to have a uniform thickness along a surface of the lower electrode 365.

The dielectric layer 370 may have a single-layered structure as illustrated in FIG. 9. In an example embodiment, the dielectric layer 370 may have a multi-layered structure.

In an example embodiment, a reflow process may be further performed to improve step coverage of the dielectric layer 370. The reflow process may be performed at a temperature ranging from about 250° C. to about 1,000° C., in one example embodiment, from about 300° C. to about 500° C.

Figure 10:
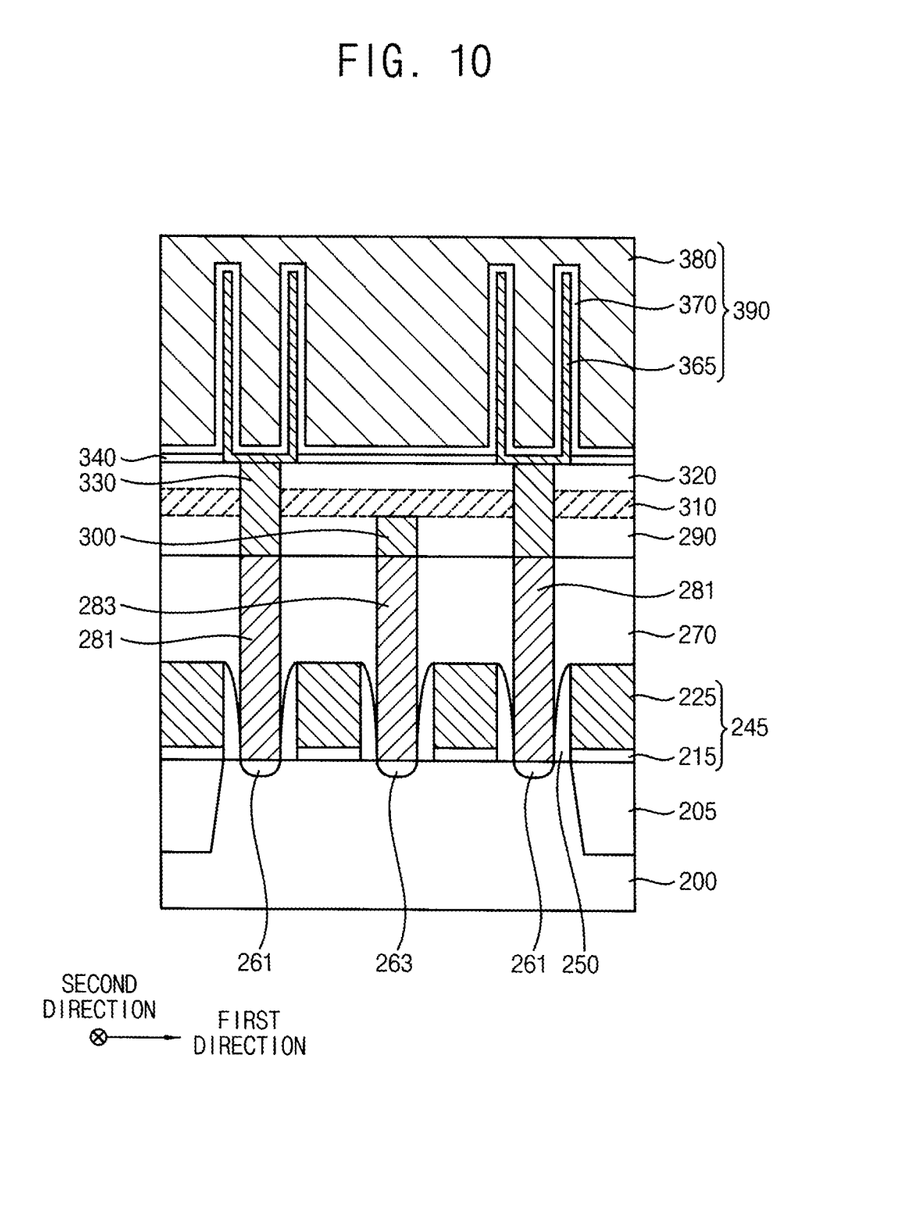

Referring to FIG. 10, an upper electrode 380 may be formed on the dielectric layer 370. Thus, a capacitor 390 including the lower electrode 365, the dielectric layer 370 and the upper electrode 380 may be obtained.

The upper electrode 380 may include a material substantially the same as or similar to the material included in the lower electrode 365. For example, the upper electrode 380 may include a metal such as tungsten, titanium or tantalum, or a metal nitride such as tungsten nitride, titanium nitride or tantalum nitride.

According to example embodiments of the present inventive concepts, the organometallic precursor as described above may have improved chemical stability, volatility, thermal stability and step coverage. Thus, a thin layer having improved electrical or dielectric properties may be formed using the organometallic precursor by, e.g., a CVD process and an ALD process.

Figure 11:
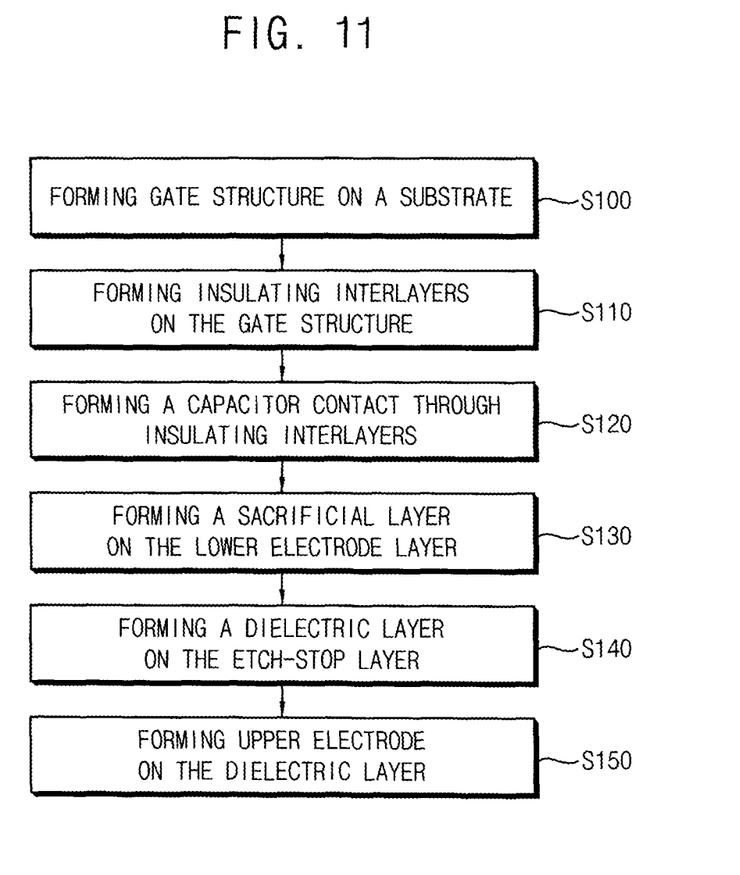
FIG. 11 is a flow chart illustrating a method of manufacturing a semiconductor device in accordance with example embodiments.

FIG. 11 is a flow chart illustrating a method of manufacturing a semiconductor device in accordance with example embodiments. In FIG. 11, the method starts at S100, where a gate structure in formed on a substrate. In S110, a first insulating interlayer is formed to cover the gate structure on the substrate. In S120, a capacitor contact is formed through insulating interlayers formed on the first insulating interlayer. In S130, a sacrificial layer is formed on the lower electrode layer formed on the sidewall and bottom of an opening formed in a mold layer on the capacitor contact. In S140, a dielectric layer is formed on an etch-stop layer formed on the capacitor contact. In S150, an upper electrode is formed on the dielectric layer.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concepts. Accordingly, all such modifications are intended to be included within the scope of the present inventive concepts as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. An organometallic precursor represented by Chemical Formula 1:

$$X_n(M)(R1)_m(R2)_k \qquad \text{[Chemical Formula 1]}$$

wherein M is a central metal,

X is a ligand of M and one of 6,6-dimethylfulvenyl, indenyl, cyclopentadienyl and cyclopentadienyl substituted with a first amino group, R1 and R2 are ligands of M, and each independently a second amino group or an ethylenediamino group, each one of n, m and k is a positive integer, and a sum of n, m and k is equal to one of 3 and 4.

2. The organometallic precursor of claim 1, wherein the central metal is one of zirconium, hafnium and titanium.

3. The organometallic precursor of claim 1, wherein the second amino group and the ethylenediamino group of R1 and R2 each independently include a $C_1$-$C_4$ alkyl substituent.

4. The organometallic precursor of claim 1, wherein X is 6,6-dimethylfulvenyl or indenyl, R1 and R2 are each independently the second amino group, n is equal to 1, and m+k is equal to 3.

5. The organometallic precursor of claim 1, wherein X comprises cyclopentadienyl substituted with the first amino group, and X is a multidendate ligand.

6. The organometallic precursor of claim 5, wherein the organometallic precursor is represented by Structural Formula 1:

[Structural Formula 1]

wherein M is a central metal, R3 and R4 are each independently methyl or ethyl, and R5 is a $C_1$-$C_4$ alkyl.

7. The organometallic precursor of claim 1, wherein R1 is the second amino group, R2 is the ethylenediamino group, and each of n, m and k is equal to 1.

8. The organometallic precursor of claim 7, wherein the organometallic precursor is represented by Structural Formula 2:

[Structural Formula 2]

wherein M is a central metal, R3 and R4 are each independently methyl or ethyl, and R6 is a C1-C4 alkyl.

9. A method of forming a thin layer, comprising:
providing a deposition source including an organometallic precursor represented by Chemical Formula 1 on a substrate; and
providing a reactive gas on the substrate to react with the deposition source, $X_n(M)(R1)_m(R2)_k$  [Chemical Formula 1]

wherein M is a central metal,
X is a ligand of M and one of 6,6-dimethylfulvenyl, indenyl, cyclopentadienyl and cyclopentadienyl substituted with a first amino group,
R1 and R2 are ligands of M, and each independently a second amino group or an ethylenediamino group, and
each of n, m and k is a positive integer, and a sum of n, m and k is equal to one of 3 and 4.

10. The method of claim 9, wherein the central metal is one of zirconium, hafnium and titanium.

11. The method of claim 10, wherein the deposition source includes at least two organometallic precursors, the central metals of which are different from each other.

12. The method of claim 9, wherein the deposition source further includes a silicon compound.

13. The method of claim 9, wherein the reactive gas includes at least one of an oxidizing agent, a reducing agent and a nitridating agent.

14. The method of claim 9, wherein the reactive gas and the deposition source are configured to react with each other at a temperature ranging from about 200° C. to about 325° C.

15. The method of claim 9, wherein the organometallic precursor includes at least one compound from a plurality of compounds represented by Structural Formulas 1 to 4:

[Structural Formula 1]

[Structural Formula 2]

[Structural Formula 3]

[Structural Formula 4]

wherein M is a central metal, R3 and R4 are each independently methyl or ethyl, and R5 and R6 are each independently a $C_1$-$C_4$ alkyl.

16. A deposition structure comprising:
a substrate;
a deposition layer on the substrate, the deposition layer including an organometallic precursor represented by the following formula:

$X_n(M)(R1)_m(R2)_k$

M being a metal,
X being a ligand of M and one of 6,6-dimethylfulvenyl, indenyl, cyclopentadienyl and cyclopentadienyl substituted with a first amino group,
R1 and R2 being ligands of M, and each independently being a second amino group or an ethylenediamino group,
each one of n, m and k being a positive integer, and a sum of n, m and k is equal to one of 3 and 4.

17. The deposition structure of claim 16, wherein a thickness of the deposition layer is substantially uniform when deposited on a concave surface.

18. The deposition structure of claim 16, wherein the metal is one of zirconium, hafnium and titanium.

19. The deposition structure of claim 16, wherein the organometallic precursor is represented by Structural Formula 1:

[Structural Formula 1]

wherein M is a central metal, R3 and R4 are each independently methyl or ethyl, and R5 is a $C_1$-$C_4$ alkyl.

20. The deposition structure of claim 16, wherein the organometallic precursor is represented by Structural Formula 2:

[Structural Formula 2]

wherein M is a central metal, R3 and R4 are each independently methyl or ethyl, and R6 is a C1-C4 alkyl.

* * * * *